(12) United States Patent
Jang

(10) Patent No.: US 9,964,462 B2
(45) Date of Patent: May 8, 2018

(54) FLEXIBLE SHEET-TYPE PHYSICAL PROPERTY DETECTING LEAK SENSOR DEVICE

(71) Applicant: FLUORO TECH CO., LTD., Gumi-si, Gyeongsangbuk-do (KR)

(72) Inventor: Moon Soo Jang, Gumi-si (KR)

(73) Assignee: FLUORO TECH CO., LTD., Gumi-si, Gyeongsangbuk-Do (KR)

( * ) Notice: Subject to any disclaimer, the term of this patent is extended or adjusted under 35 U.S.C. 154(b) by 0 days. days.

(21) Appl. No.: 15/501,455

(22) PCT Filed: Aug. 14, 2015

(86) PCT No.: PCT/KR2015/008541
§ 371 (c)(1),
(2) Date: Feb. 3, 2017

(87) PCT Pub. No.: WO2016/024850
PCT Pub. Date: Feb. 18, 2016

(65) Prior Publication Data
US 2017/0227415 A1  Aug. 10, 2017

(30) Foreign Application Priority Data

Aug. 14, 2014  (KR) .......................... 10-2014-0105714

(51) Int. Cl.
*G01M 3/16* (2006.01)
*G01M 3/40* (2006.01)
*G01R 19/145* (2006.01)
*G01R 19/15* (2006.01)
(Continued)

(52) U.S. Cl.
CPC .............. *G01M 3/165* (2013.01); *G01M 3/16* (2013.01); *G01M 3/40* (2013.01); *G01N 17/02* (2013.01);
(Continued)

(58) Field of Classification Search
CPC .......... G01M 3/00; G01M 3/007; G01M 3/04; G01M 3/165; G01M 3/40; G01R 19/00;
(Continued)

(56) References Cited

U.S. PATENT DOCUMENTS 5,904,426 A * 5/1999 Tsuru ...................... F16C 33/62
384/462
2008/0061458 A1 * 3/2008 Park ........................ B29C 33/62
264/1.32
(Continued)

FOREIGN PATENT DOCUMENTS

JP          07325056 A     12/1995
JP       2005164366 A      6/2005
(Continued)

OTHER PUBLICATIONS

International Search Report dated Nov. 24, 2015 for PCT/KR2015/008541 and English translation.

*Primary Examiner* — Hoai-An D Nguyen
(74) *Attorney, Agent, or Firm* — Lucas & Mercanti, LLP

(57) ABSTRACT

A flexible sheet-type leak sensor device according to the present invention comprises: a flexible base sheet made of a non-conductive fluorine-based synthetic resin comprising ethylene tetrafluoroethylene (ETFE); conductive lines formed on a surface of the base sheet so as to have a predetermined pattern and so as not to meet or cross each other, the conductive lines being formed by depositing on the base sheet surface a carbon black-containing, conductive fluorine-based synthetic resin comprising ethylene tetrafluoroethylene (ETFE); and a conductive material composed of pure carbon black, formed at the bottom of the conductive lines.

4 Claims, 2 Drawing Sheets

(51) Int. Cl.
*G01R 19/155* (2006.01)
*G01N 17/02* (2006.01)

(52) U.S. Cl.
CPC ............ *G01R 19/145* (2013.01); *G01R 19/15* (2013.01); *G01R 19/155* (2013.01)

(58) Field of Classification Search
CPC ............ G01R 19/0084; G01R 19/0092; G01R 19/154; G01R 19/15; G01R 19/155; G01R 19/165; G01R 27/00; G01R 27/08; G01R 27/26; G01R 31/00; G01R 31/08; G01R 31/10; G01R 31/28; G01R 31/2812; G01N 17/00; G01N 17/006; G01N 17/02; G01N 17/04; G01N 27/00; G01N 27/02; G01N 27/025; G01N 27/04
USPC ....... 324/600, 649, 691, 693, 713, 715, 718, 324/500, 512, 522, 525, 527, 528, 71.1, 324/71.2
See application file for complete search history.

(56) References Cited

U.S. PATENT DOCUMENTS

| | | | | |
|---|---|---|---|---|
| 2008/0121740 | A1* | 5/2008 | Yamada | B05B 5/04 239/703 |
| 2014/0210603 | A1* | 7/2014 | Walser | B60Q 9/00 340/438 |
| 2016/0166757 | A1* | 6/2016 | Koyama | G01M 3/16 324/693 |
| 2016/0282216 | A1* | 9/2016 | Lee | G01M 3/16 |

FOREIGN PATENT DOCUMENTS

| | | |
|---|---|---|
| KR | 1020040076576 A | 9/2004 |
| KR | 100909242 B1 | 7/2009 |
| KR | 1020110007501 A | 1/2011 |
| KR | 101020377 B1 | 3/2011 |
| KR | 101326923 A | 11/2013 |

* cited by examiner

[Figure 1]
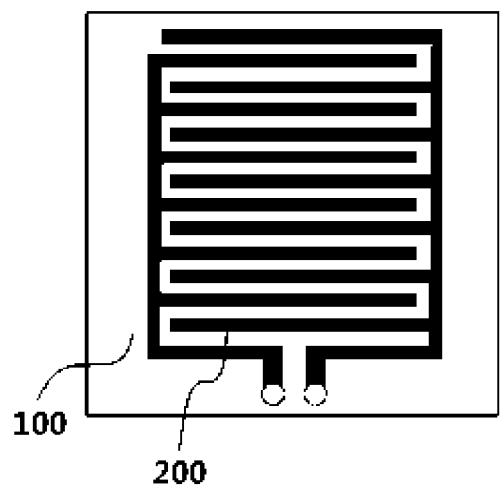

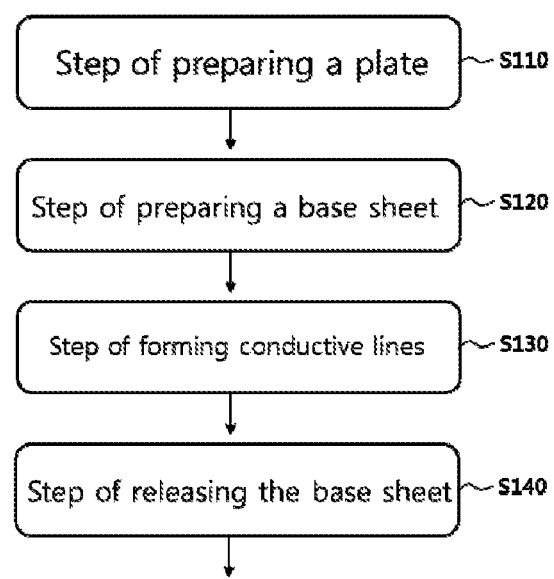

FLEXIBLE SHEET-TYPE PHYSICAL PROPERTY DETECTING LEAK SENSOR DEVICE

CROSS-REFERENCE TO RELATED APPLICATIONS

This application is a 371 of PCT/KR2015/008541, filed Aug. 14, 2015, which claims the benefit of KR 10-2014-0105714 filed Aug. 14, 2014, the contents of each of which are incorporated herein by reference.

TECHNICAL FIELD

The present invention relates to a flexible sheet-type leak sensor device, and more particularly, to a flexible sheet-type leak sensor device, comprising: a flexible base sheet made of a non-conductive fluorine-based synthetic resin comprising ethylene tetrafluoroethylene (ETFE); and conductive lines famed on a surface of the base sheet so as to have a predetermined pattern and so as not to meet or cross each other, the conductive lines being formed by depositing on the base sheet surface a carbon black-containing, conductive fluorine-based synthetic resin comprising ethylene tetrafluoroethylene (ETFE).

BACKGROUND ART

Various types of leak sensors for detecting water and oil leaks have been used. Typical examples of the leak sensors include a cable-type leak sensor, a band-type leak sensor and a module-type leak sensor.

The cable-type leak sensor is a water and oil leak detection sensor for detecting the exposure of various types of liquid (e.g., water and oil) and accurately and rapidly informing the location of liquid leaks. When an electric current flows through a conducting wire, a potential difference is generated by the resistance of leaked water or oil. This potential difference can be detected using a detection line, thereby making it possible to check water and oil leaks. However, this cable-type leak sensor requires high installation costs, and the consumer's selection of the cable-type leak sensor is limited because the sensor cable has a determined length. Furthermore, there are problems in that, because a separate bracket should be used for installation of the sensor, it is difficult to install the sensor and an additional cost is incurred, and in that a large amount of time is required to remove a leak after detection of the leak and it is difficult to connect the cable-type leak sensor to an external device.

In the case of the band-type leak detection sensor, when water comes in contact with an electric wire when an electric current flows through the electric wire, the resistance value of the electric wire will change. Based on this change in the resistance value, the band-type leak detection sensor can detect water leaks. This band-type leak detection sensor can detect water leaks in a large area at low costs and is easily installed. However, it has problems in that the incidence of error due to high humidity and external impact is high, the accurate location of water leaks cannot be easily checked, and it is difficult to install the sensor because it lacks the connection of installation. In addition, there are problems in that the price versus performance of the band-type leak detection sensor is high, and a bracket has to be fixed to the bottom needs to be installed separately, making it difficult to install the sensor. In addition, there is a problem an alternative connection device in addition to a simple relay contact point method is not present when connecting the band-type leak sensor to an external device.

The module-type leak sensor includes photo sensors (e.g., a light-receiving unit and a light-emitting unit) within a plastic casing. The light-receiving unit receives a beam from the light-emitting unit in a state in which liquid is not detected. However, when the beam of the light-emitting unit detects liquid, the beam does not enter the light-receiving unit due to a change in the refractive index. Thus, the leak sensor detects water leaks in a state in which light is received. This module-type leak sensor can detect portions, which are at risk of water leaks, at low costs, is easily installed, can generate an alarm by itself regardless of the surrounding device, and does not show an error attributable to humidity. However, the module-type leak sensor has problems in that it can detect only a water leak at a specific location, unlike the cable-type leak detection sensor, and it is difficult to connect the module-type leak sensor with the surrounding device. In addition, there are problems in that, because a separate sensor fixing scheme should be planned, a large amount of time is required to install the module type leak sensor, and because only a specific portion in an area being at risk of water leaks can be detected, detection becomes difficult if the location of water leaks is changed.

PRIOR ART DOCUMENTS

Patent Documents

Patent Document 1: Korean Unexamined Patent Application Publication No. 10-2011-0007501 (published on Jan. 24, 2011);

Patent Document 2: Korean Patent No. 10-1326923 (registered on Nov. 1, 2013).

DISCLOSURE

Technical Problem

The present invention is directed to a flexible sheet-type leak sensor device, comprising: a flexible base sheet made of a non-conductive fluorine-based synthetic resin comprising ethylene tetrafluoroethylene (ETFE); and conductive lines famed on a surface of the base sheet so as to have a predetermined pattern and so as not to meet or cross each other, the conductive lines being formed by depositing on the base sheet surface a carbon black-containing, conductive fluorine-based synthetic resin comprising ethylene tetrafluoroethylene (ETFE).

Technical Solution

The present invention has been made in order to solve the above-described problems and limitations occurring in the prior art, and it is a major object of the present invention to provide a flexible sheet-type leak sensor device having the advantages of a cable-type leak sensor together with the advantages of a band-type leak sensor.

Another object of the present invention is to provide a flexible sheet-type leak sensor device capable of detecting even minute leaks, which could not be recognized and detected by conventional leak sensors, in which the flexible sheet-type leak sensor device does not show a dead point (referring to a location that causes poor reception in a wireless system) and is highly sensitive.

Still another object of the present invention is to provide a flexible sheet-type leak sensor device which is made of a fluorine-based synthetic resin having strong resistance to acidic or alkaline compounds, and thus can be reused again as a sensor device after simple removal of a leaked solution without being damaged by leak detection even when the leaked solution is an acidic solution containing hydrofluoric acid, sulfuric acid, nitric acid or the like.

Advantageous Effects

The flexible sheet-type leak sensor device according to the present invention is made of Teflon that is a fluorine-based synthetic resin which is not damaged even by acidic solutions and alkaline solutions. Thus, the flexible sheet-type leak sensor device has advantages in that it can safely detect a leak without misoperation, even when the leaked material is strongly acidic or alkaline, and in that it can be reused again after removal of the leaked material contaminating the sensor device.

Furthermore, the flexible sheet-type leak sensor device according to the present invention has a simple structure and is also configured such that it can accurately detect the leakage of materials having various physical properties by merely controlling the spacing and width of conductive lines. Thus, it has the advantages of a cable-type leak sensor together with the advantages of a band-type leak sensor which has a simple structure while being inexpensive.

Meanwhile, according to a method for manufacturing a flexible sheet-type leak sensor device according to the present invention, a solid-state fluorine-based synthetic resin and a liquid-state fluorine-based synthetic resin, which are difficult to combine with each other, can be combined by sintering. Thus, the method according to the present invention has an advantage in that it can manufacture a flexible sheet-type leak sensor device which has excellent acid resistance and physical properties, can accurately detect leaks, substantially shows no dead point, and is highly sensitive.

DESCRIPTION OF DRAWINGS

FIG. 1 shows the overall structure of a flexible sheet-type leak sensor device according to the present invention.

FIG. 2 shows a process for manufacturing a flexible sheet-type leak sensor device according to the present invention.

DESCRIPTION OF REFERENCE NUMERALS

100: base sheet;
200: conductive lines;
S110: a step of preparing a plate;
S120: a step of preparing a base sheet;
S130: a step of forming conductive lines;
S140: a step of releasing the base sheet.

MODE FOR INVENTION

Hereinafter, embodiments of the present invention will be described in detail with reference to the accompanying drawings.

FIG. 1 shows the overall structure of a flexible sheet-type leak sensor device according to the present invention.

A base sheet 100 is prepared using a non-conductive, non-adhesive fluorine-based synthetic resin such as ethylene tetrafluoroethylene (ETFE). When the base sheet is made of ethylene tetrafluoroethylene (ETFE), conductive lines 200 are generally formed by printing a liquid ethylene tetrafluoroethylene (ETFE) resin, which contains 15 wt % or less of carbon black as a conductive material, on the prepared 250 μm thick film by a metal masking method to form patterns, and then calcining the printed resin.

Although not specifically shown in FIG. 1, carbon black that is a conductive material is formed at the bottom of the conductive lines 200.

The operation of the flexible sheet-type leak sensor device according to the present invention is as follows. When leaked liquid falls onto the surface of the sensor, the conductive lines 200, which are formed to be spaced apart from each other and electrically isolated from each other, communicate to each other by the leaked liquid so that electricity flows through the conductive lines. When this electric current passage occurs, the sensor detects the electric current passage, thereby indicating that a water leakage or liquid leakage from a flange or the like occurred in an area in which the sensor is located.

Meanwhile, after the occurrence of a liquid leakage was confirmed, the sensor can function again as a sensor by merely removing the leaked liquid without having to replace the sensor. Thus, the sensor device according to the present invention does not need to be replaced after detection of water or liquid leaks, and can be used in a semi-permanent way after installation.

In addition, the sensor device according to the present invention has a flexible structure that can be wound around a flange or the like to detect liquid leaks. Thus, it has advantages in that installation of the sensor is easy and no dead point occurs.

EXAMPLE

In the example of the present invention, a flexible sheet-type leak sensor device was manufactured in which the base sheet 100 and the conductive lines 200 were all made of ethylene tetrafluoroethylene (ETFE). The base sheet 100 was formed to have a thickness of 250 μm, and the conductive lines 200 were formed to have a thickness of 100 μm. The conductive ethylene tetrafluoroethylene (ETFE) resin used contained 15 wt % of acetylene black. Specifically, distilled water, a stearic acid compound, a glycol compound and sorbitan were prepared in a beaker, and a non-conductive ethylene tetrafluoroethylene (ETFE) resin solution was added thereto. Glycerin was added to the beaker, and carbon black consisting of a mixture of acetylene black and lamp black was added to the beaker, followed by ultrasonic mixing.

In this example, acetylene black that is a conductive material was famed at the bottom of the conductive lines 200. Specifically, the conductive material was prepared by adding a small amount of an aceto-orcein solution to acetylene black, neutralizing the mixture with DI water to form a paste, and adding a small amount of a dispersing agent to the paste to disperse the paste at a high density. Acetylene black prepared in a paste state was printed on the surface of the base sheet 100 by use of a metal mask so as to have a small width (width: 900 μm; height 15 μm), and the above-prepared conductive ethylene tetrafluoroethylene (ETFE) resin was deposited thereon so as to have a slightly wider width (width: 1100 μm; height: 25 μm), thereby forming a two-layer structure. Next, the resulting structure was dried at room temperature for about 1 hour, and then sintered at 300° C. for about 10 minutes, thereby forming an integrated structure. As a result, conductive lines 200 could be obtained, which have a thickness of 40 μm and include the conductive material carbon black formed at the bottom.

The flexible sheet-type leak sensor device manufactured according to the present invention had a size of 50 cm (width)×50 cm (length) and showed a detection resistance of 200-300 kΩ over the total area of the sensor device.

FIG. 2 shows a process for manufacturing a flexible sheet-type leak sensor device according to the present invention.

As shown in FIG. 2, step S110 of preparing a plate is a step of subjecting the surface of a metal plate to shot blasting, and then coating the surface with liquid polytetrafluoroethylene (PTFE), followed by sintering, thereby preparing a plate for sheet preparation, the surface of which has a release property. The polytetrafluoroethylene (PTFE) can be securely fixed to the surface of the metal plate, and thus a plate for sheet preparation, the surface of which has a release property, can be prepared.

Step S120 of preparing a base sheet is a step of applying non-conductive ethylene tetrafluoroethylene (ETFE) powder to the surface of the plate coated with polytetrafluoroethylene (PTFE), and heat-treating the applied powder, thereby preparing a base sheet 100 made of ethylene tetrafluoroethylene (ETFE). Because ethylene tetrafluoroethylene (ETFE) has the characteristics of thermoplastic resin, the ethylene tetrafluoroethylene powder is heat-treated to prepare a sheet. Herein, the heat treatment is preferably performed once or more at a temperature of 310 to 320° C.

Step S130 of forming conductive lines is a step of depositing a conductive ethylene tetrafluoroethylene (ETFE) containing carbon black on the surface of the base sheet 100 by a metal masking method, thereby forming conductive lines 200 patterned so as not to meet or contact each other.

Step S140 of releasing the base sheet is a step of separating the base sheet 100, which has the conductive lines 200 formed thereon, from the plate for sheet preparation.

Through the above-described steps, a flexible sheet-type leak sensor device made of ethylene tetrafluoroethylene (ETFE) is manufactured.

INDUSTRIAL APPLICABILITY

As described above, the flexible sheet-type leak sensor device according to the present invention is made of Teflon that is a fluorine-based synthetic resin which is not damaged even by acidic solutions and alkaline solutions. Thus, the flexible sheet-type leak sensor device can safely detect a leak without misoperation, even when the leaked material is strongly acidic or alkaline, and it can be reused again after removal of the leaked material contaminating the sensor device. Furthermore, the flexible sheet-type leak sensor device according to the present invention has a simple structure and is also configured such that it can accurately detect the leakage of materials having various physical properties by merely controlling the spacing and width of conductive lines. Thus, it has the advantages of a cable-type leak sensor together with the advantages of a band-type leak sensor which has a simple structure while being inexpensive. Meanwhile, according to the method for manufacturing the flexible sheet-type leak sensor device according to the present invention, a solid-state fluorine-based synthetic resin and a liquid-state fluorine-based synthetic resin, which are difficult to combine with each other, can be combined by sintering. Thus, the method according to the present invention can manufacture a flexible sheet-type leak sensor device which has excellent acid resistance and physical properties, can accurately detect leaks, substantially shows no dead point, and is highly sensitive.

The invention claimed is:

1. A flexible sheet-type leak sensor device, comprising:
   a flexible base sheet made of a non-conductive fluorine-based synthetic resin comprising ethylene tetrafluoroethylene (ETFE);
   conductive lines formed on a surface of the base sheet so as to have a predetermined pattern and so as not to meet or cross each other, the conductive lines being formed by depositing on the base sheet surface a carbon black-containing, conductive fluorine-based synthetic resin comprising ethylene tetrafluoroethylene (ETFE); and
   a conductive material composed of pure carbon black, formed at a bottom of the conductive lines.

2. The flexible sheet-type leak sensor device of claim 1, wherein a content of the carbon black in the conductive fluorine-based synthetic resin forming the conductive lines is 15 wt % or less.

3. The flexible sheet-type leak sensor device of claim 1, wherein a width of the conductive lines is 0.1-5 mm, and a spacing between the conductive lines is 0.5-3 mm.

4. The flexible sheet-type leak sensor device of claim 1, wherein the base sheet has a thickness of 100-300 μm.

* * * * *